United States Patent
Silansky et al.

(10) Patent No.: US 12,009,103 B1
(45) Date of Patent: Jun. 11, 2024

(54) SYSTEMS, DEVICES, AND/OR METHODS FOR MANAGING HEALTH (71) Applicants: Edward R Silansky, Reston, VA (US); Jennifer Finan, Warrenton, VA (US); Leslie Ricci, Stephens City, VA (US)

(72) Inventors: Edward R Silansky, Reston, VA (US); Jennifer Finan, Warrenton, VA (US); Leslie Ricci, Stephens City, VA (US)

( * ) Notice: Subject to any disclaimer, the term of this patent is extended or adjusted under 35 U.S.C. 154(b) by 0 days.

(21) Appl. No.: 17/192,547

(22) Filed: Mar. 4, 2021

(51) Int. Cl.
G16H 50/30 (2018.01)
G06F 21/62 (2013.01)
G16H 10/60 (2018.01)
G16H 20/60 (2018.01)
G16H 50/20 (2018.01)

(52) U.S. Cl.
CPC .......... G16H 50/30 (2018.01); G06F 21/6245 (2013.01); G16H 10/60 (2018.01); G16H 20/60 (2018.01); G16H 50/20 (2018.01)

(58) Field of Classification Search
CPC ........ G16H 50/30; G16H 10/60; G16H 20/60; G16H 50/20; G06F 21/6245
See application file for complete search history.

(56) References Cited

U.S. PATENT DOCUMENTS

| | | | |
|---|---|---|---|
| 2008/0208619 A1* | 8/2008 | Swanson | G16H 40/20 705/2 |
| 2009/0187420 A1* | 7/2009 | Hancock | G16H 20/60 705/2 |
| 2011/0208659 A1* | 8/2011 | Easterly | G06Q 20/3274 705/79 |
| 2015/0248651 A1* | 9/2015 | Akutagawa | G06F 16/2465 705/7.19 |
| 2015/0332020 A1* | 11/2015 | Lo | A61B 5/1079 702/19 |
| 2017/0166848 A1* | 6/2017 | Toumazou | C12Q 1/6844 |
| 2017/0251985 A1* | 9/2017 | Howard | G16H 70/60 |
| 2020/0273578 A1* | 8/2020 | Kutzko | H04L 9/3239 |

* cited by examiner

Primary Examiner — Fekadeselassie Girma
Assistant Examiner — Mancil Littlejohn, Jr.

(57) ABSTRACT

Certain exemplary embodiments can provide a method. The method can comprise causing a first user interface to be automatically rendered on a device via an App. The first user interface can comprise health instructions. The health instructions can be rendered responsive to a communication from a server to the App. The communication from the server comprises the health instructions. The health instructions can be determined via the server based upon an Artificial Intelligence algorithm.

20 Claims, 3 Drawing Sheets

SYSTEMS, DEVICES, AND/OR METHODS FOR MANAGING HEALTH

CROSS-REFERENCES TO RELATED APPLICATIONS

This application claims priority to, and incorporates by reference herein in its entirety, U.S. Provisional Patent Application Ser. No. 62/984,940, filed Mar. 4, 2020.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Certain exemplary embodiments can provide a method. The method can comprise causing a first user interface to be automatically rendered on a device via an App. The first user interface can comprise health instructions. The health instructions can be rendered responsive to a communication from a server to the App. The communication from the server comprises the health instructions. The health instructions can be determined via the server based upon an Artificial Intelligence algorithm.

Certain exemplary embodiments provide a method constructed to alter certain human behavior in order to achieve outcomes that improve the health of users. Certain exemplary embodiments can utilize technology in new and focused ways that, over time, and with built in support devices, encourages users to stay engaged and in doing so, changes their health profile and feel that they accomplished something of value for themselves and those they are close to. Certain exemplary embodiments utilize machine learning, which can provide a precise roadmap for each individual to achieve a healthier life no matter their age or current health condition. When coupled with unique tools that reinforce behavioral change, certain exemplary embodiments attempt to motivate each user to continue one or more programs designed for them, such that outcomes are much improved. Certain exemplary embodiments integrate machine learning with an individual health profile that includes DNA along with video analytics to produce a localized process to impact behavior on a sustainable basis.

Figure 1:
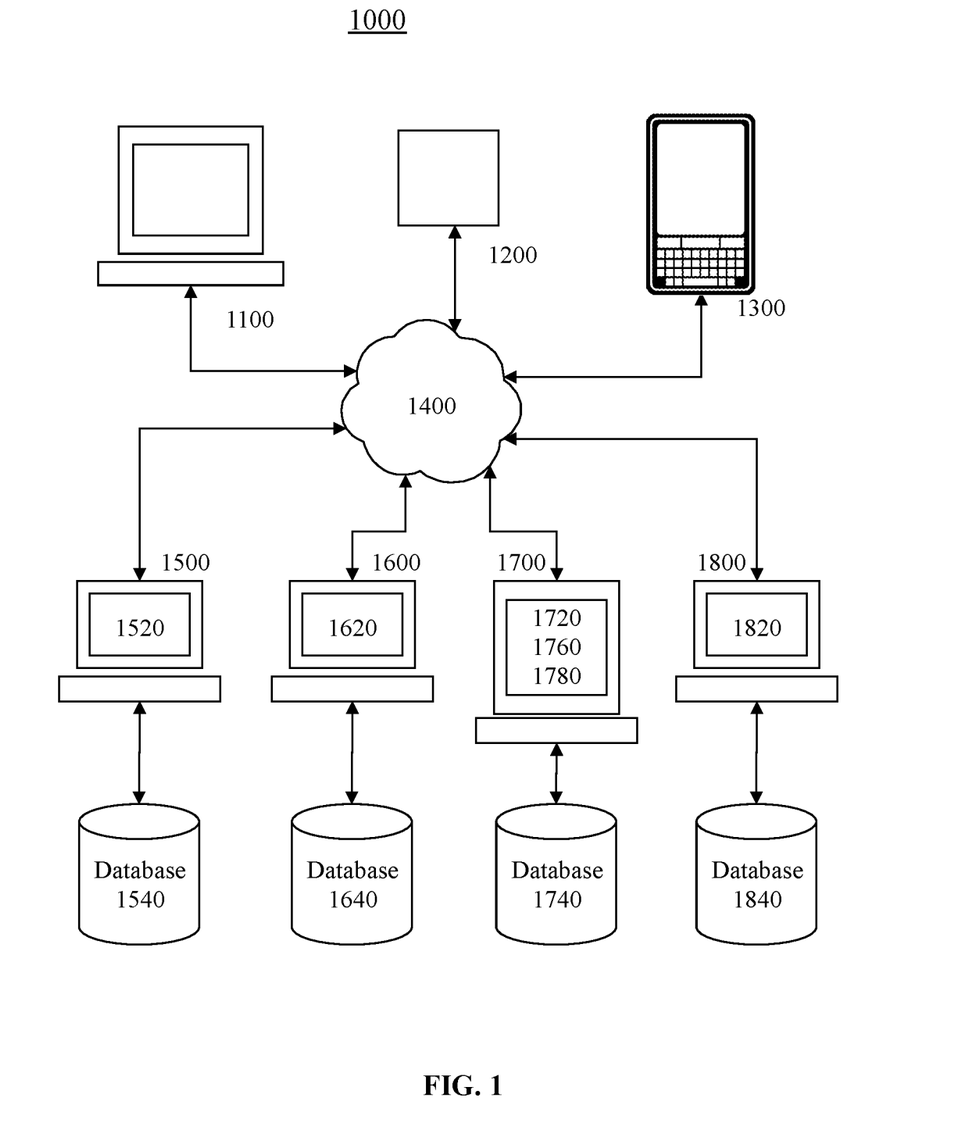
FIG. 1 is a block diagram of an exemplary embodiment of a system 1000.

FIG. 1 is a block diagram of an exemplary embodiment of a system 1000, which can comprise a smartphone 1300, an information device 1100, tablet 1200, a network 1400, a first server 1500, a second server 1600, a third server 1700, and a fourth server 1800. First server 1500 can comprise a first user interface 1520 and can be coupled to a first database 1540. Second server 1600 can comprise a second user interface 1620 and can be coupled to a second database 1640. Third server 1700 can comprise a third user interface 1720, a processor 1760, machine instructions 1780, and can be coupled to a third database 1740. Fourth server 1800 can comprise a fourth user interface 1820 and can be coupled to a fourth database 1840. Any of the methods and/or steps thereof can be carried out in whole or in part by tablet 1200, smartphone 1300, information device 1100 and/or first server 1500. Second server 1600, third server 1700, and/or fourth server 1800 can each be associated with implementation of a system via which human behavior can be altered. In certain exemplary embodiments, system 1000 can be used to implement one or more methods disclosed herein.

Figure 2:
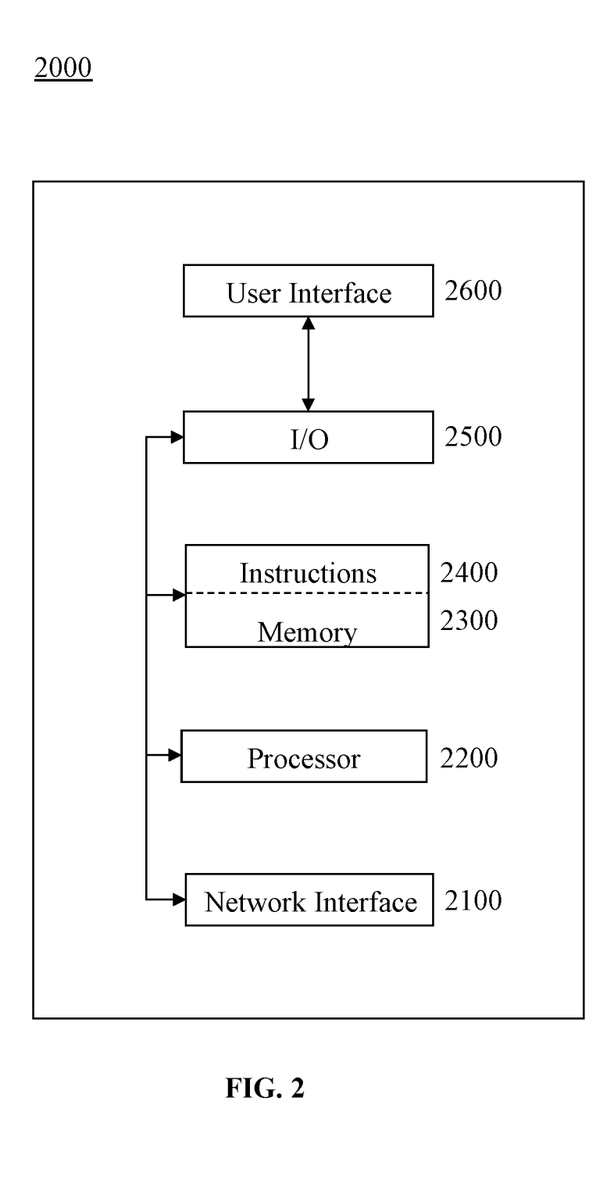
FIG. 2 is a block diagram of an exemplary embodiment of an information device 2000.

FIG. 2 is a block diagram of an exemplary embodiment of an information device 2000, which in certain operative embodiments can comprise, for example, first server 1500 and information device 1100, of FIG. 1. Information device 2000 can comprise any of numerous circuits and/or components, such as for example, one or more network interfaces 2100, one or more processors 2200, one or more memories 2300 containing instructions 2400, one or more input/output devices 2500, and/or one or more user interfaces 2600 coupled to one or more input/output devices 2500, etc.

In certain exemplary embodiments, via one or more user interfaces 2600, such as a graphical user interface, a user can view a rendering of information related to researching, designing, modeling, creating, developing, building, manufacturing, operating, maintaining, storing, marketing, selling, delivering, selecting, specifying, requesting, ordering, receiving, returning, rating, and/or recommending any of the products, services, methods, and/or information described herein.

Figure 3:
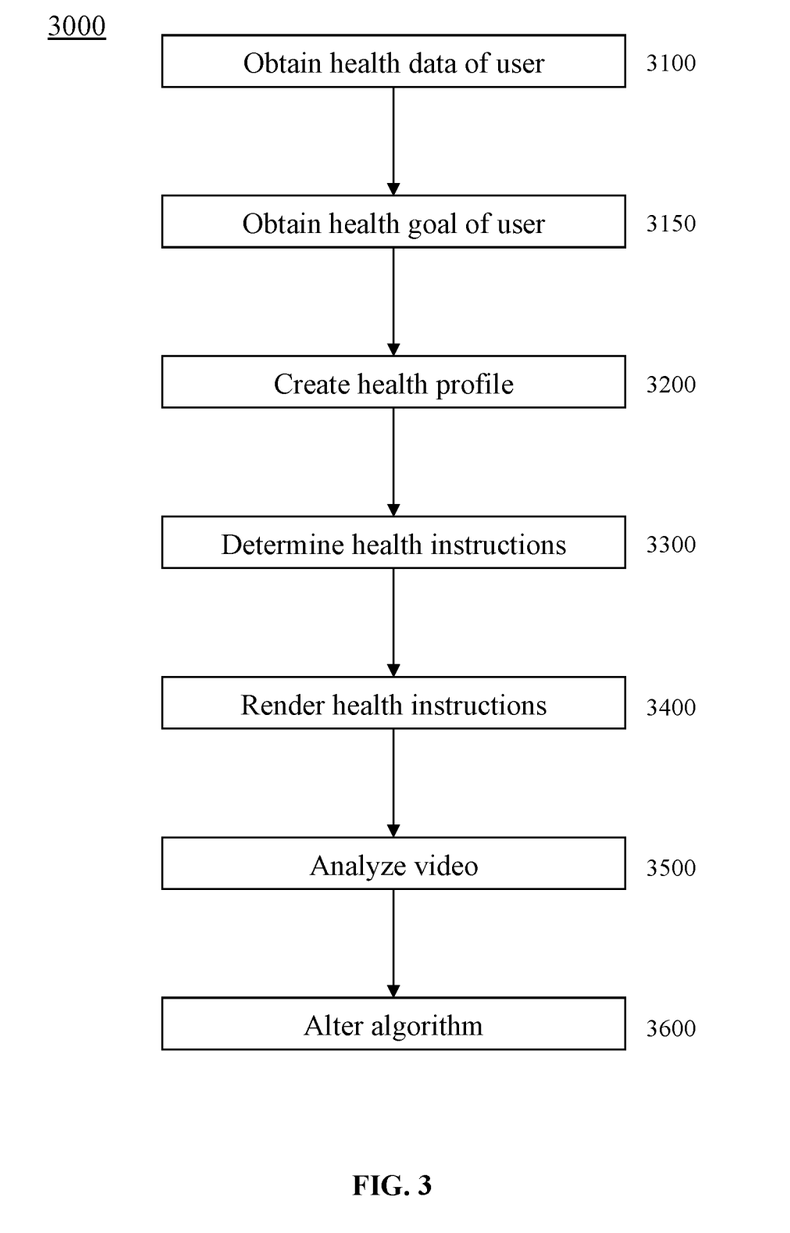
FIG. 3 is a flowchart of an exemplary embodiment of a method 3000.

FIG. 3 is a flowchart of an exemplary embodiment of a method 3000. At activity 3100, health data of a user can be obtained. Certain exemplary embodiments can cause a health information user interface to be automatically rendered on a device via an App. The health information user interface can request and/or obtain health information from the user, such as via a health information user interface of the App. In certain exemplary embodiments, health information regarding the user can be obtained from medical databases, physician records, clinic records, gym records, and/or dietetic records, etc. Certain exemplary embodiments can utilize DNA analytic data as health data.

At activity 3150, a health goal of the user can be obtained. A second user interface to be automatically rendered on the device via the App. The second user interface can request and obtain an input of one or more health goals by the user.

At activity 3200, a health profile of the user can be created. The health profile of the user can be automatically determined from the health data of the user. The health profile can comprise an automatic analysis of DNA of the user. The automatic analysis of the DNA can identify markers indicative of health risks and/or potential morbidities for the user.

At activity 3300, health instructions can be determined automatically at the server. The health instructions can be determined via the server based upon an Artificial Intelligence algorithm. The Artificial Intelligence algorithm can utilize the health profile of a user to automatically determine the health instructions. The health profile comprises the goal of the user. In certain exemplary embodiments, the health instructions are based upon an automatic DNA analysis by the Artificial Intelligence algorithm. The health instructions can be communicated from the server to the App via an encrypted transmission.

At activity 3400, health instructions can be rendered. Certain exemplary embodiments can cause a first user interface to be automatically rendered on a device via an App. The first user interface comprises the health instructions. The health instructions can be rendered responsive to a communication from a server to the App. The communication from the server comprising the health instructions. Certain exemplary embodiments can cause a health instructions user interface to be automatically rendered via the App.

In certain exemplary embodiments, the health instructions are exercise instructions. The exercise instructions can be determined based upon an automatic determination of a location of the user. In such embodiments, the health instructions might suggest that the user utilize a particular gym and/or perform a particular set of exercises.

In certain exemplary embodiments, the health instructions are dietary instructions. The health instructions user interface can recommend a dining location and/or a food to be eaten by the user. The health instructions user interface can recommend an exercise location. The health instructions user interface can recommend a dietician. The health instructions user interface can be rendered in consideration of, and/or responsive to, an automatically determined location of the user.

In certain exemplary embodiments, the health instructions user interface can provide health risk information for the user based upon an automatic DNA analysis by the Artificial Intelligence algorithm. The health instructions user interface can provide a probability of a health outcome for the user based upon the automatic DNA analysis by the Artificial Intelligence algorithm. The health instructions user interface can provide a probability of a health outcome for the user based upon the health profile of the user.

In certain exemplary embodiments, the health instructions user interface can recommend a medical test. The health instructions user interface can comprise locations of providers capable of performing the medical test. The locations of providers can be automatically rendered responsive to location information of the user. In certain exemplary embodiments, the health instructions user interface can recommend the user have a DNA test.

In certain exemplary embodiments, the health instructions user interface can provide information to the user concerning another person with a similar health profile of the user. The health instructions user interface can provide an option to initiate contact with the another person.

At activity 3500, a video of the user can be automatically capture, transmitted, and analyzed. In certain exemplary embodiments, data can be added to the health profile of the user. The data can be indicative of progress of the user toward the goal of the user. In other embodiments, the data can be obtained from a medical examination of the user.

At activity 3600, the Artificial Intelligence algorithm can be altered. The Artificial Intelligence algorithm can be altered based upon an automatic analysis of facial expressions detected in a video of the user that was automatically transmitted from the App to the server. In subsequent repetitions of activity 3300 and other activities, the health instructions can be determined via the altered Artificial Intelligence algorithm. In such embodiments, the health instructions are different than would have been transmitted to the user interface prior to the Artificial Intelligence algorithm having been altered. In certain exemplary embodiments, the Artificial Intelligence algorithm is altered for the user based upon an automatic DNA analysis identifying health risks of the user.

Exemplary methods for DNA analysis can be found in U.S. Patent Publication 2020/0347461, which is incorporated by reference in its entirety.

Processing can be used to determine if someone has health risks or morbidities by utilizing or performing any of the following, but not limited to: waveform analysis, filtration (band pass filtration, finite/infinite response filters, adaptive filters, Gabor filters, and/or other filters), decimation, Hilbert transformation, deconvolution, wavelet denoising, time series analysis, empirical mode decomposition, confidence intervals, normalization/standardization, significance testing, stochastic modeling, machine learning (deep learning, artificial neural networks, and other types of learning), iterative reconstruction, fast-Fourier transform (FFT), compressed sensing, expectation-maximization algorithm, averaging, probability distributions, standard deviation, slope, bootstrapping, and/or pattern recognition, etc. Other mathematical or statistical tools can be used to achieve the same goal as certain embodiments without departing from the spirit and scope thereof.

A wide variety of analytical techniques can be applied to current and/or historical data concerning the health of the user, such as, for example, probability analyses (e.g., a priori probabilities, conditional probabilities, and/or posteriori probabilities, etc.), distribution analysis, sampling theory, classification analysis (e.g., Bayesian Decision Theory, parametric techniques (such as Bayesian estimation, maximum likelihood estimation, and/or Markov models, etc.), non-parametric techniques (such as Parzen windows, nearest neighbor, etc.), linear discriminant techniques, neural networks, stochastic methods, nonmetric methods, algorithm-independent machine learning, and/or unsupervised learning and/or clustering), correlation theory and/or analysis (e.g., curve fitting, regression, multiple correlation, and/or partial correlation, etc.), analysis of variance, analysis of time series (e.g., smoothing, moving averages, trend estimation, estimation of seasonal variations and/or seasonal index, deseasonalization, estimate of cyclic variations, and/or estimate of irregular variations, etc.), forecasting, queuing theory, decision theory, and/or information theory.

Certain exemplary embodiments provide application software (an "App") linked to a wearable device, e.g., an iPhone (iPhone is a registered trademark of Apple Inc. of Cupertino, California), and a secure/encrypted connection to an Artificial Intelligence ("AI" or machine learning) host that takes basic health information as provided by users including DNA screens, one or more goals sought by users based upon their respective current health profile and develops a holistic, data driven health plan for each user that is unique to them. AI allows the App to develop a unique roadmap for each user, based upon their health data as provided, suggest additional testing to track/disclose potential issues flagged by DNA markers and other health data, suggest food items/meals to support the wellness of the user which are improved by a local dietician and an exercise routine to be done at a gym or at home and when undertaken, puts the user on a path to "be all you are able" to be, and feel good about doing so. Adding results to the profile as the user follows the roadmap and giving feedback on results and new medical data as provided shows, in real time, the progress being made and such data can be used by users' doctors and others to engage with better knowledge of individual patients and what will improve outcomes. Over time, the App collects a wealth of information about outcomes of changing behavior based upon the best science available and is made precise to each individual as AI allows. More importantly, the DNA analysis, when coupled with other health data like blood profiles, when fed into an AI data base of like profiles, can determine precise health risks of each user and suggest further testing, and/or changed behavior.

What this process design accomplishes is to provide a roadmap for well being using technology that then gets implemented on a location by location basis to build local support tools/relationships/education that is unique to both the individual and the community.

Ongoing improvements in AI enable novel approaches to health care that focus on prevention rather than reactions to illnesses that occur after people are ill or are in less than optimal health. Historically much of the efforts of health care have been focused on treating patients after they show symptoms or suffer from some major health event. Treatment and medications for the most part deal with and are focused on controlling conditions after the fact. The outcomes of this approach are pretty clear. Over 68% of U.S. citizens are deemed to be obese or overweight. More children than ever are suffering from diabetes and for the first time in history, life expectancies are declining. Yet people spend billions of dollars each year on diet plans and rush to buy the latest "new thing" that claims to be healthy or promote weight loss. It is also of interest that there are about 40,000 health clubs/gyms in the US with a total membership of about 50 million who spend some $26 billion to be members. A reasonable question to ask is: if we as a country are spending some $70 billion per year for just diet and exercise programs, why are we as a nation less healthy with average life expectancies and illnesses occurring in children at earlier ages?

The answer to this worsening situation is not complicated to define, but it is hard to remedy. More than 40% of all users to a diet plan or a health club drop out after 6 months because they do not have the support tools that allow for sustainable behavioral change. Certain exemplary embodiments address such issues via integrating the best analytics as to a person's health profile with support tools that reinforce continued engagement, so that over time, behavior is altered.

The science to understand how to lead a healthy life is pretty clear and has been for some time. Certain exemplary embodiments utilize AI/machine learning to analyze large bodies of data available on any given health issue and make available to the average person methods that can lead to optimal outcomes based upon sustainable changes in human behavior. AI also can utilize analytics of volumes of health data on a given subject and based upon such analytics, can predict with some measurable probability, health outcomes of individuals with the same or similar characteristics, as algorithms produced from the analytics allow such understanding. What no one doubts any longer is that diet and exercise done in the right way, help promote better health in general. In addition, and in the privacy of one's own home, an individual can take a DNA test which provides a wealth of data regarding certain health indicators and also undertake, either at gyms in each city where the App is deployed, or doctors' offices, a wide range of tests that allow a full profile of most, if not all health data that enables the establishment of a health baseline for each person. With full encryption of data associated with each person, the data is secured and provides information for reference and use of exemplary AI components. Certain exemplary embodiments provide a method based upon a health profile of each user, suggest things that could be investigated by doctors, and/or suggest behavior changes that could help alter and improve the health profile for every user. Moreover, AI allows the App to be utilized to track in a very objective manner how people view their well-being over time based upon an analysis of facial markers over the course of a particular activity or participation in a health-based program as provided by the App described herein. In other words, exemplary methods allow each person to see in real time how they feel about what they have accomplished by adhering to the plan developed for them. When coupled with video content that tracks facial markers as taken over the course of the program, each user can see and even measure the impact the program has had on how they feel about what they have done and/or are currently doing. Facial expression analysis is an indicator tracked over time to reflect how one feels about the progress toward a goal being accomplished. Other indicators which might support an outcome comprise weight, skin tone, bodyshape and/or medical test results measured over time, etc. All such indicators can be used as markers of progress to the goal.

Certain exemplary embodiments provide a method tailored to each user and their precise health profile, from a genetic marker that may predict a health problem, to recovering from major health issue (e.g., a heart attack). By employing AI to a particular condition to learn best practices which is then analyzed by the AI host to create a baseline program of additional testing to undertake, diet, and exercise which all are specific to each user, certain exemplary embodiments are able to be both proactive and focused on what may well be life altering behavior. Certain exemplary methods can enhance a user's determination to stay the course.

As the App user base expands, exemplary methods track data from persons with similar conditions and/or defects indicated from DNA and can determine which characteristics produce the best results as can be determined via the App. Such a constant feedback loop between the AI host and the user, improves the algorithms and makes them more reliable, which in turn produces better outcomes for the users with similar issues.

What is becoming clear, and as is the case with lipoprotein (a) ("LPa"), as an example, there are genetic markers that provide clues to a possible medical problem and when detected should encourage more tests to better define the risk factors and to suggest modified behavior, including a change in diet and exercise. This process starts with a baseline of data for each user, who will be encouraged to undertake a DNA analysis, allows the App to better understand the linkage between DNA and pre-dispositions to multiple health issues. AI allows the App to first identify a precise DNA marker, research all the data on the topic and produce an algorithm for predictive outcomes where that marker is indicated. In one application for an exemplary method, what the App seeks to do is to collect data from users with a given marker and suggest additional testing as indicated by the data and then to alter diet and exercise based upon analytics of baseline health data. As new data is provided to the host from the users as to the health profile for each person, analytics can track changes based upon changed behavior and over time produce algorithms based upon the new data. Given sufficient users with similar health profiles or where a DNA analysis has been done, the App can track changes in the health profile based upon modified behavior and over time demonstrate the impact the altered behavior has produced in the user base with similar baseline health data. Further, the collection of this data over time can be shared with users' health providers (e.g., doctors and/or specialists, etc.) to provide better care, which can be focused on prevention rather than recovery. Certain exemplary embodiments provide an information loop between the AI analytics and users, which produce better algorithms that predict outcomes based upon behavioral change. Properly incentivized, such loops produce better information, which in turn results in better outcomes. Certain exemplary methods create a support mechanism to stay engaged.

Since certain exemplary embodiments are deployed locally, a hands-on local support group can be linked through the App so those with common issues can support one another as they undertake improvement efforts. The App is designed to build linkages locally via linking local gyms, physical therapy providers, vendors, and/or local meal preparation so there is a sense of community with positive reinforcement. Many people who join a gym drop out after relatively short time periods and the same holds true for those on various diet programs. By creating local support and reinforcement, the app facilitates building a community that celebrates progress and better outcomes long term.

Built into the App are features that enable communities to compete with one another on identified goals and, based upon outcomes, reward prizes to the user base in one community to go to their selected local cause, be it a charity or a local project. Events get recorded by a video method that follows the outcome over time and then is posted on the host cloud site and shared with other communities.

Today more than 28 million people have undergone DNA testing and several vendors provide a health marker kit for various types of issues that are disclosed by the DNA test. This is but one part of the process described in this filing. With the knowledge of a predisposition, family history (e.g., like heart attacks, cancer, diabetes, etc.), and current medical testing that gets associated with the DNA results, the App can suggest three or more things that allow the user to take control of his/her health and do so at any age. Those things can comprise:

- additional testing based upon the DNA results;
- a diet tailored to the profile that addresses issues which can be improved and/or altered; and/or
- an exercise program designed to maximize health at any age and/or condition.

Certain exemplary embodiments are not only constructed for use each person, but also link local users to an integrated support process to encourage continual reinforcement of the altered behavior so that the user is doing this as a part of a community that celebrates/recognizes improved outcomes over time.

An Exemplary Process:

In a selected population center, the App can select a gym or a plurality of gyms based upon population to offer a service that allows the integration of elements that comprise:

- A base line health analysis of each App user. This will include for example, a DNA profile, baseline health indicators like blood analysis, heart health/EKG/BP, weight, age, allergies, prior medical issues, to create a current health profile, medical indicators and goals of the individual. All data is secure/encrypted and confidential and as the user becomes trusting of the process and as recommended, they may add to the data provided. The more data the more reliable the program/outcomes.
- With the data provided, AI analytics, and based upon a machine learning process, many of which have already been undertaken, by multiple sources, will suggest things, which can comprise:
  - Additional tests as suggested by the science for whatever issue the user is dealing with.
  - Certain food items that address the improvement of the user's health profile. AI providers have already done this analysis and it is readily available.
  - Based upon the genetic testing and the health profile, a combination of supplements and/or vitamins that address precisely the condition/s that the user is dealing with.
- An activity program to achieve the goal of each user, both at gyms where they are members and/or when at home.
- A video analytics capability that can, as undertaken by users, record visual changes in users over time, record facial markers that show emotion over time and track those changes (i.e., deltas) that show objectively how users feel about what they have done.

Based upon one or more of the suggestions and goals of each user, the App can suggest food items. The food items can be determined via an AI analysis that measures nutritional values that should be eaten daily to help improve health precisely indicated by the analysis and will also suggest an initial exercise program which will be updated and modified over time based upon the data that is recorded and fed into personal profiles on the APP by users. The App can utilize real-time processing that tracks and reports back to each user the impact of changed behavior on demand from App users, or periodically and/or automatically so users are aware of changes in conditions.

The App can take food items for each category like vegetables, protein, carbs, and/or juices etc. and use AI to create menu suggestions for meals to be eaten each day. The App host can engage a local dietician to sample and improve the items and add a personal touch to improve flavor and variety (certain exemplary AI algorithms can comprise thousands of menu items and/or recipes online). This is a part of a "keep it local" program as without a local support process and feedback, data shows that people simply drop out and revert to old behaviors.

Each user, based upon a personal profile, can use the App to order meals tailored to meet the nutritional profile as provided by the AI generated analytics for one day or one week; and each order is sent to a local mobile kitchen for preparation or to a local restaurant that has been identified by the App.

Each user ordering can pick up a particular order from any preselected location around a town and/or city at times predetermined so it is a convenience and not a hassle. This is done via the App. The difference from other plans is the items are all prepared fresh and with local sources, where possible, so the meals are made within a few hours of consumption. Users can order a meal cooked for immediate consumption or simply assembled to be prepared later. The user can place orders any time of the day and designate pick up location according to a schedule set by the kitchens employed. This is like a grocery store on wheels except each meal is selected precisely based upon improving the health profile of the user and the AI source tracks all meals purchased and stores the data and uses same to follow the progress of things like weight, blood sugar levels, heart rates, blood pressure, and/or other vitals that are indicative of improvements in overall health.

Based upon baseline health profiles and goals of each user, the App can suggest an exercise routine for each category of user. For example, the App can define broad categories of health issues such as recovering from a heart attack to reducing risk of diabetes, losing weight, improving skin tone, and/or appearance depending upon goals. It is also the case that the DNA analysis may disclose certain pre-dispositions that were not known to users and those marker profiles can be included in the selection of both diet and exercise for each user as well as recommended additional tests to better define health issues. As a general matter, the more one knows about their baseline health profile, the more proactive they can become because they better understand the risk factors they may be dealing with. Further, the App can break down each group of local users into criteria that apply to a subset in each group such as those who had a heart attack before the age of 50 and those that had one after 50—this is simply an example of what criteria can be used to become more precise in the recommended diet and exercise program prepared for each user. An objective is to make outcomes as personal and precise as science allows such that users recognize that what is suggested is tailored for her or him.

One of advantages of certain exemplary embodiments is the ability to tailor solutions to each individual based upon the science for each, not some general sense of well, if I do this or take that I will feel better. This is clearly the case with those who take some vitamin and/or mineral supplements daily, not knowing for certain the impact of doing so and the reasons for it. Certain exemplary Apps provide a feature that takes the health profile, including the genetic analytics, does a search of all precise vitamins and supplements recommended by the science that deal with a precise condition or pre-condition, and then recommends a precise powder or pill that contains the right supplement and in the right dose. Such embodiments provide a powder and/or pill that combines the right items and in the right dosages.

At each gym associated with the App, the App can set appointments with trainers and/or trained personnel of the gyms to accomplish one or more of:

Go through a listing of data that should be collected to establish the health base line and allow the user the choice of what they would like to provide. This can be as little as weight and blood pressure or as much as a full-blown compliment of data that comprises DNA. There are sources available for such data from accessible by the App (e.g., trainers taking tests, doctors' records, and/or off-site testing, etc.). As users see progress, they may wish to add to the data base they provide and such is encouraged—more data, better results. All data collected is sent securely to the AI host via encryption methods and stored according to a unique identifier for each user. As the program continues over time new tests will be suggested to mark deltas in health data and make changes to diets and exercise based upon those deltas. The App can provide to each user, as requested via a click button, both graphic and numeric tracking over time so each user can view progress and the impact that changes to the program of diet and exercise have altered results. The App can also suggest when users should undertake other and/or additional testing based upon the analytics of users. The App is a pro-active health care tool to address issues that may impact health in the future.

Users, once the base line data is collected, set goals that they have for better health and the initial time period to achieve it. This can be as simple as losing 30 pounds to a heart patient wanting to be able to walk a mile without stopping or a marathon runner getting ready for a race. More to the point, any genetic marker discovered in the testing process and from which additional testing is suggested, the analytics provided might disclose conditions the user was not even aware of. With knowledge of the condition the user is able to alter behavior and testing to avert a health crisis and to share such information with their health care providers.

In certain exemplary embodiments, the App can select food items to be used and an exercise program to undertake for each user. The App tracks exercise, meals consumed and health indicators during the day and sends all data to the AI host and the App prompts a weekly update using certain health markers that demonstrate progress and/or changes.

Certain exemplary embodiments provide a "mood measurement" feature, which records the user's face to analyze the various mood indicators that are well understood to record a baseline for what the user is feeling at the beginning of the program. As users request, they can take periodic photos/videos as prompted by the App to track changes in mood and/or happiness based upon the progress being made with the program designed for that user and the AI host will measure those changes and provide a visual graph to the user so they can see, over time, changes in mood and/or happiness with the progress they are making. This feature becomes a self-motivating tool and can be shared with friends and other users of the App to feel proud of the progress made and promotes the continued use of the APP until defined goals are achieved. The user can then set new goals or simply engage in a maintenance program to stay as fit/healthy as they wish to be. Measuring objectively how you are feeling about yourself based upon activities undertaken, is a human motivator which encourages users to stay engaged.

Well defined goals based upon a baseline unique to each user that are incorporated into a holistic system of diet, exercise, monitoring, and/or emotional feedback that can be done at a gym or at home, provides users tools to take control of their health, monitor it in real time, track their progress, and share that progress visually and graphically with others to gain positive reinforcement.

Baseline health profiles for each user that are generated and are analyzed by the App based upon data, provides a proactive way to take control of users' full medical profiles and not be reactive to health changes, often times with less than optimal outcomes.

As the user base expands, trainers can form groups that fall into categories of health and goals and create teams to work together and to compete with other teams both locally and in other locations. The App can establish a rewards program for winners over periods of time and social media efforts to celebrate outcomes.

The App can provide, via AI analysis, video analytics where videos are taken of users who seek to improve their performance and such videos can be compared to AI data on the same subject and an overlay allows users to see how what they do compares with the best way or the way a world class performer does the same exercise. This way, users can better understand how to achieve better results and can be encouraged to continually seek to be better. It matters not if this to simply help the heart patient walk a mile without stopping or high jumper training for the Olympics. It is a feedback loop that is a positive reinforcer of working to get better as it relates to each personal goal.

It is also clear that the composition of all the food we consume has various nutrients of different values and health impact and AI allows the App to provide information about all the things that anyone might consume and understand the health/benefit impact of each. Using AI, the App can construct a list of foods that support whatever health goals each user may have as long as parameters are set correctly. A borderline diabetic knows foods consumed make a difference in sugar levels. High blood pressure individuals also know food intake can help lower not only blood pressure but also improve the HDL/LDL ratio. AI can provide a list of all foods that support more healthy blood sugar levels. The issue is how to get those impacted to consume what is good for them. The App utilizes a process, which allows a direct link among the user, the recommended foods consumed and an easy direct way to have available the very same day, prepared meals that support a healthy diet. Alternatively, the user can take the suggested food items and alter what meals he or she prepares at home.

Certain exemplary embodiments provide an interactive App, which incorporates a detailed health profile of each user as provided under strict confidentiality conditions, with goals set by each user such as reducing blood sugar levels, improving blood profile/triglycerides, losing 25 pounds, etc. The App can suggest foods to include in a diet and an exercise program for each user, based upon all of the data previously collected and analyzed. The App undertakes an analysis of foods available in the marketplace and this information can be used to prepare meals. The App can prepare menus, which are available on line so the capability exists to take the approved foods for each condition or goal and with the involvement of a dietician employed by the host, create meals for each user group that can vary by taste, ethnic preferences, or other criteria. Dieticians can direct tastings to ensure high quality and variety for each user group. The daily menus can be available as a download on the App for each user so that at any time, be it during the work out or at the office, each user can order meals. Local food trucks and/or restaurants can be associated with the App. Staff on such trucks can receive the orders and pick-up times. Such trucks can have a defined route in each town/city to ensure convenience. Certain exemplary embodiments provide delivery services that allow precisely tailored meals to be prepared as ordered and available within a couple of hours of the order being placed. Users can order each day so that meals are fresh and tailored to each user. Menu items can be tailored to goals of each participant and it is likely that the participants in each city where the program is deployed will fall into one or more predetermined categories, and menu offerings can be designed to address the most common characteristics that apply to multiple users. Certain exemplary embodiments can be utilized to motivate a local population to achieve better health. Certain exemplary embodiment can provide a city by city program, which relies upon members of the local population who are concerned about achieving better health, no matter the age or condition of the users. The App can establish relationships with local gyms or conditioning clubs and even physical therapy providers in each city where the App is utilized. Information can comprise health information, DNA testing, and/or medical test results, etc. The App can interact gym personnel and/or each member to set the exercise routine as established by the App. Each user can utilize a mobile device that records activity, calories burned, and allows the user to place meal orders and/or set pick up times. Calories for each meal can be recorded on the system.

The App can create in one place a complete health program that can be used by anyone regardless of age, health condition, health goals, conditioning objectives that is fully integrated, easy to use, and allows every participant to receive support and feedback as to progress, factors to improve exercise routines and meals that are tailored to the taste and health needs of each user.

AI elements allow individual analysis of health profiles of each user with as much data as the user wishes to provide and the output is a food and exercise program that takes that data and the goal of each user to create a daily food intake and exercise routine that is monitored by a worn device. All such data is sent to the App to track progress and revise each as changes occur. All of this data is available to the user so they can see the progress and modify the program as they wish.

Definitions

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.
activity—an action, act, step, and/or process or portion thereof.
adapted to—made suitable or fit for a specific use or situation.
adapter—a device used to effect operative compatibility between different parts of one or more pieces of an apparatus or system.
add—to include something.
algorithm—a finite sequence of well-defined, computer-implementable instructions that achieves conditional results.
alter—to change.
analysis—an evaluation.
and/or—either in conjunction with or in alternative to.
another person—a human other than a user.
apparatus—an appliance or device for a particular purpose.
application ("App")—machine instructions that perform a particular task or set of tasks.
artificial intelligence ("AI")—machine instructions resulting in an information device with a capacity for logic, understanding, self-awareness, learning, emotional knowledge, reasoning, planning, creativity, critical thinking, and problem solving.
artificial neural network ("ANN")—a real or virtual device in which several interconnected elements process information simultaneously, adapting and learning from past patterns. Not necessarily a "network" as defined herein.
associate—to join, connect together, and/or relate.
attempt—to try to do something.
automatically—acting or operating in a manner essentially independent of external influence or control. For example, an automatic light switch can turn on upon "seeing" a person in its view, without the person manually operating the light switch.

based upon—used as a criterion for a determination.

can—is capable of, in at least some embodiments.

capable—having an ability to do something.

cause—to bring about.

circuit—an electrically conductive pathway and/or a communications connection established across two or more switching devices comprised by a network and between corresponding end systems connected to, but not comprised by the network.

communication—a data transmission.

complete—substantially whole or entire.

comprising—including but not limited to.

configure—to make suitable or fit for a specific use or situation.

confirm—to acknowledge with definite assurance.

constructed to—made to and/or designed to.

convert—to transform, adapt, and/or change.

couple—to link in some fashion.

data—distinct pieces of information, usually formatted in a special or predetermined way and/or organized to express concepts.

decision tree—a tree algorithm in which the selection of each branch requires that some type of logical decision be made.

dietary instructions—directions regarding food recommended for human consumption.

different—not the same as.

define—to establish the outline, form, or structure of.

detect—to sense or perceive.

determine—to obtain, calculate, decide, deduce, and/or ascertain.

device—a machine, manufacture, and/or collection thereof.

dietician—an expert on diet and nutrition.

diet program—a deliberate selection of food to control body weight or nutrient intake.

dine—to eat.

DNA—a nucleic acid that carries the genetic information in the cell and is capable of self-replication and synthesis of RNA. DNA consists of two long chains of nucleotides twisted into a double helix and joined by hydrogen bonds between the complementary bases adenine and thymine or cytosine and guanine. The sequence of at least certain portions of the nucleotides determines individual hereditary characteristics. Also called deoxyribonucleic acid.

eat—to consume food.

encrypt—to change data from one form to another especially to conceal a meaning of the data.

estimate—to calculate and/or determine approximately and/or tentatively.

exercise—a deliberate selection of bodily activities.

exercise program—a deliberate selection of bodily activities that enhance and/or maintain physical fitness and/or overall health and wellness.

exercise instructions—directions concerning selection of bodily activities.

food—any nutritious substance that people or animals eat or drink or that plants absorb in order to maintain life and growth.

generate—to create, produce, give rise to, and/or bring into existence.

Global Positioning System ("GPS")—a system adaptable to determine a terrestrial location of a device receiving signals from multiple satellites.

goal—an aim or desired result of a person's effort.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

health—a physical state of a human.

health conditions—characteristics of a physical state of a human.

health instructions—suggestions of actions that, when taken, will be likely to improve a condition of a human.

health outcome—a consequence pertaining to a physical state of a human.

health profile—data regarding a condition of a particular human.

health risk information—data pertaining to an adverse event or negative health consequence due to a specific event, disease, or condition.

identifier—data that is uniquely associated with a person. For example, an identifier can comprise a name, an address identified via a GPS signal, a social security number, a driver's license number, a credit card number, a debit card number, a card with a magnetic strip and/or machine-readable chip, a bracelet, and/or any object comprising a Radio-frequency identification ("RFID") tag, etc.

identify—recognize a particular person or thing.

indicative—signifying.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

input—a signal, data, and/or information provided to a processor.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

location—a place substantially approximating where something physically exists.

machine instructions—directions adapted to cause a machine, such as an information device, to perform one or more particular activities, operations, or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine readable medium—a physical structure from which a machine can obtain data and/or information. Examples include a memory, punch cards, etc.

may—is allowed and/or permitted to, in at least some embodiments.

medical examination—an evaluation of a human performed to detect, diagnose, or monitor diseases, disease processes, susceptibility, or to determine a course of treatment.

medical test—a procedure performed to detect, diagnose, or monitor diseases, disease processes, susceptibility, or to determine a course of treatment.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, ethernet card, cable modem, digital user line interface, bridge, hub, router, or other similar device.

perform—to accomplish something.

personal computing device—an information device small enough to hold and operate in a user's hand.

personal information—data that is unique to a particular individual. For example, name, address, phone number, e-mail address, credit card number, and/or a photographic image, etc.

plurality—the state of being plural and/or more than one.

portion—a part of a whole.

predetermined—established in advance.

probability—a likelihood of something happening.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, California. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

progress—to advance toward a goal.

project—to calculate, estimate, or predict.

provide—to furnish, supply, give, and/or make available.

provider—a person or legal entity that furnishes or supplies something.

receive—to get as a signal, take, acquire, and/or obtain.

recommend—to suggest, praise, commend, and/or endorse.

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

request—to express a desire for and/or ask for.

responsive—reacting to an influence and/or impetus.

server—an information device and/or software that provides some service for other connected information devices via a network.

set—a related plurality.

signal—information, such as machine instructions for activities and/or one or more letters, words, characters, symbols, signal flags, visual displays, and/or special sounds, etc. having prearranged meaning, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

store—to place, hold, and/or retain data, typically in a memory.

substantially—to a great extent or degree.

system—a collection of mechanisms, devices, machines, articles of manufacture, processes, data, and/or instructions, the collection designed to perform one or more specific functions.

toward—in a direction of.

transmit—to send as a signal, provide, furnish, and/or supply.

user—a person interfacing with an information device.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

utilize—to put to use.

via—by way of and/or utilizing.

video—a sequential set of images that, when rendered, can be seen by a human or animal and that, when rendered sequentially at a determined rate, appear to a human as if one or more things are moving.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

no characteristic, function, activity, or element is "essential";

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A method comprising:
causing a first user interface to be automatically rendered on a device via an App, the first user interface comprising health instructions, the health instructions rendered responsive to a communication from a server to the App, the communication from the server comprising the health instructions, the health instructions determined via the server based upon an Artificial Intelligence algorithm, the Artificial Intelligence algorithm utilizing a health profile of a user to automatically determine the health instructions, the health profile comprising a goal of the user, the Artificial Intelligence algorithm altered based upon an automatic analysis of facial expressions detected in a video of the user that was automatically transmitted from the App to the server, the health instructions determined via the altered Artificial Intelligence algorithm, the health instructions different than would have been transmitted to the first user interface prior to the Artificial Intelligence algorithm having been altered.

2. The method of claim 1, further comprising:
causing a second user interface to be automatically rendered on the device via the App, the second user interface requesting an input of one or more health goals by the user, the one or more health goals comprising the goal of the user.

3. The method of claim 1, further comprising:
causing a second user interface to be automatically rendered on the device via the App, the second user interface requesting health information from the user.

4. The method of claim 1, further comprising:
causing a generation of the health profile of the user, the health profile comprising an automatic analysis of DNA of the user.

5. The method of claim 1, further comprising:
causing a second user interface to be automatically rendered via the App, the second user interface requesting information from the user concerning health of the user.

6. The method of claim 1, further comprising:
causing a second user interface to be automatically rendered via the App, the second user interface recommending a dining location and a food to be eaten by the user, the second user interface rendered responsive to an automatically determined location of the user.

7. The method of claim 1, further comprising:
causing a second user interface to be automatically rendered via the App, the second user interface recommending an exercise location, the second user interface rendered responsive to an automatically determined location of the user.

8. The method of claim 1, further comprising:
causing a second user interface to be automatically rendered via the App, the second user interface recommending a dietician, the second user interface rendered responsive to an automatically determined location of the user.

9. The method of claim 1, further comprising:
causing a second user interface to be automatically rendered via the App, the second user interface providing health risk information for the user based upon an automatic DNA analysis by the Artificial Intelligence algorithm.

10. The method of claim 1, further comprising:
causing a second user interface to be automatically rendered via the App, the second user interface providing a probability of a health outcome for the user based upon an automatic DNA analysis by the Artificial Intelligence algorithm.

11. The method of claim 1, further comprising:
causing a second user interface to be automatically rendered via the App, the second user interface providing a probability of a health outcome for the user based upon the health profile of the user.

12. The method of claim 1, further comprising:
causing a second user interface to be automatically rendered via the App, the second user interface recommending a medical test, the second user interface comprising locations of providers capable of performing the medical test, the locations of providers automatically rendered responsive to location information of the user.

13. The method of claim 1, further comprising:
adding data to the health profile of the user, the data indicative of progress of the user toward the goal of the user, the data obtained from a medical examination of the user.

14. The method of claim 1, further comprising:
causing a second user interface to be automatically rendered via the App, the second user interface recommending a DNA test.

15. The method of claim 1, further comprising:
causing a second user interface to be automatically rendered via the App, the second user interface providing information to the user concerning another person with a similar health profile of the user, the second user interface providing an option to initiate contact with the another person.

16. The method of claim 1, wherein:
the health instructions are based upon an automatic DNA analysis by the Artificial Intelligence algorithm.

17. The method of claim 1, wherein:
the Artificial Intelligence algorithm altered for the user based upon an automatic DNA analysis identifying health risks of the user.

18. The method of claim 1, wherein:
the health instructions are dietary instructions.

19. The method of claim 1, wherein:
the health instructions are exercise instructions, the exercise instructions determined based upon an automatic determination of a location of the user.

20. The method of claim 1, wherein:
the health instructions are communicated from the server to the App via an encrypted transmission.

* * * * *